(12) United States Patent
Eberle

(10) Patent No.: US 11,007,530 B2
(45) Date of Patent: May 18, 2021

(54) HOLDER FOR RECEIVING AND STORING LABORATORY VESSELS

(71) Applicant: Andreas Hettich GmbH & Co. KG, Tuttlingen (DE)

(72) Inventor: Klaus-Günter Eberle, Tuttlingen (DE)

(73) Assignee: ANDREAS HETTICH GmbH & CO. KG, Tuttlingen (DE)

( * ) Notice: Subject to any disclaimer, the term of this patent is extended or adjusted under 35 U.S.C. 154(b) by 357 days.

(21) Appl. No.: 15/567,673

(22) PCT Filed: Apr. 22, 2016

(86) PCT No.: PCT/EP2016/059089
§ 371 (c)(1),
(2) Date: Oct. 19, 2017

(87) PCT Pub. No.: WO2016/170161
PCT Pub. Date: Oct. 27, 2016

(65) Prior Publication Data
US 2018/0117594 A1  May 3, 2018

(30) Foreign Application Priority Data

Apr. 24, 2015 (DE) .................... 10 2015 207 617.2

(51) Int. Cl.
*B01L 9/00* (2006.01)
*C12M 1/22* (2006.01)
(Continued)

(52) U.S. Cl.
CPC ........ *B01L 9/52* (2013.01); *B01L 9/06* (2013.01); *C12M 23/10* (2013.01); *C12M 23/48* (2013.01);
(Continued)

(58) Field of Classification Search
None
See application file for complete search history.

(56) References Cited

U.S. PATENT DOCUMENTS

| 617,478 A | * | 1/1899 | Cohen ...................... A47F 5/01 |
| | | | 211/49.1 |
| 3,830,701 A | | 8/1974 | Stussman et al. |
| (Continued) | | | |

FOREIGN PATENT DOCUMENTS

| DE | 103 01 446 A1 | 7/2004 |
| DE | 20 2005 017 383 U1 | 1/2006 |
| (Continued) | | |

OTHER PUBLICATIONS

International Search Report and Written Opinion dated Jul. 28, 2016, issued in counterpart PCT application PCT/EP2016/059089.
(Continued)

*Primary Examiner* — Kathryn Wright
(74) *Attorney, Agent, or Firm* — Juan Carlos A. Marquez; Marquez IP Law Office, PLLC

(57) ABSTRACT

A holder (10) receives and stores laboratory vessels for samples, microorganisms, cell cultures or the like, with a housing (14), and at least one receptacle (20) for the laboratory vessels. The receptacle (20) extends along a loading axis (L) in the housing (14) and is configured such that the laboratory vessels can be introduced into the receptacle (20) and can be stacked on top of each other therein, wherein the receptacle (20) in the housing (14) has a loading opening (20a) to permit loading. On an underside (18) arranged remote from the loading opening (20a), the receptacle (20) has an unloading opening (20b), which can be closed by means of a closure mechanism (38) arranged in the housing (14). The closure mechanism (38) is provided with a slide (40, 42), via which the slide (40, 42) is movable to
(Continued)

the unloading opening (20b) to permit closure and is movable from the unloading opening (20b) to an opening position to permit opening.

16 Claims, 3 Drawing Sheets

(51) Int. Cl.
*C12M 3/00* (2006.01)
*B01L 9/06* (2006.01)
*C12M 1/00* (2006.01)
*G01N 35/00* (2006.01)

(52) U.S. Cl.
CPC ........ *C12M 99/00* (2013.01); *B01L 2200/025* (2013.01); *B01L 2200/028* (2013.01); *B01L 2200/12* (2013.01); *B01L 2200/18* (2013.01); *B01L 2300/021* (2013.01); *B01L 2300/045* (2013.01); *B01L 2300/0832* (2013.01); *B01L 2300/0851* (2013.01); *G01N 2035/00801* (2013.01)

(56) References Cited

U.S. PATENT DOCUMENTS

| | | | |
|---|---|---|---|
| 4,143,765 A | | 3/1979 | Moss, III |
| 4,558,802 A | * | 12/1985 | Molison ............... B65G 47/514 |
| | | | 221/104 |
| 2006/0211080 A1 | | 9/2006 | Frost, III et al. |
| 2012/0175328 A1 | | 7/2012 | Bosch |
| 2017/0254826 A1 | * | 9/2017 | Eberle .............. G01N 35/00871 |

FOREIGN PATENT DOCUMENTS

| | | |
|---|---|---|
| EP | 0 242 114 A2 | 10/1987 |
| EP | 1 018 544 A1 | 7/2000 |
| EP | 1 445 309 A1 | 8/2004 |

OTHER PUBLICATIONS

German Search Report dated Feb. 19, 2016, issued in counterpart German Patent Application No. 10 2015 207 617.2.

\* cited by examiner

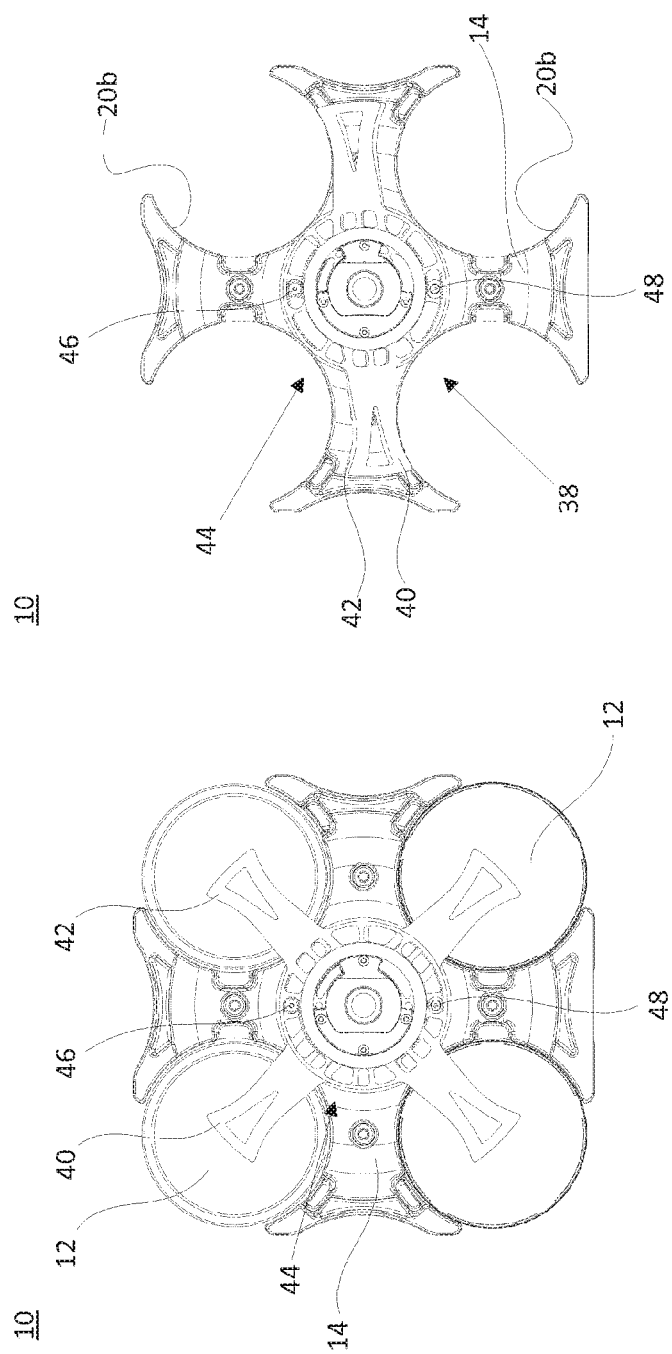

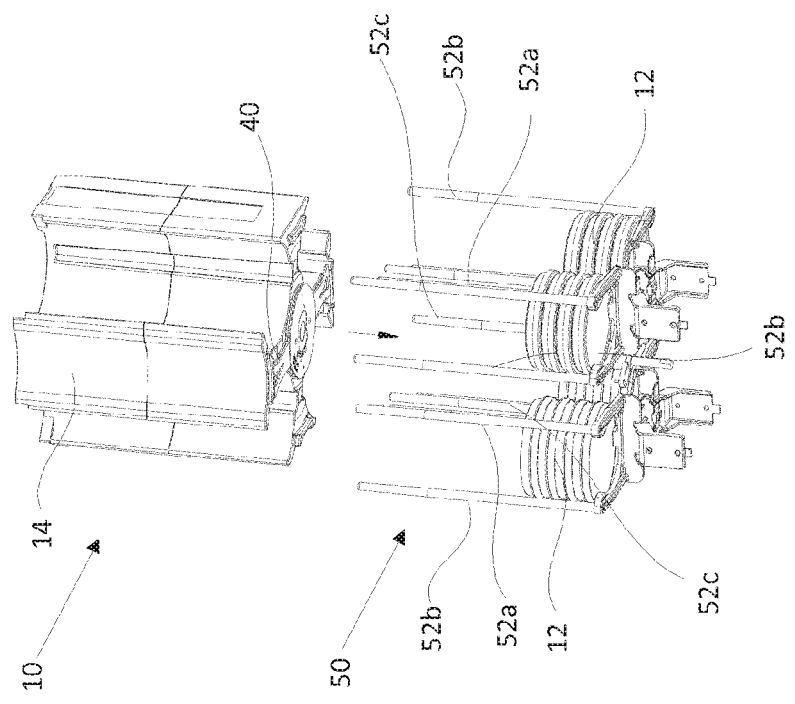
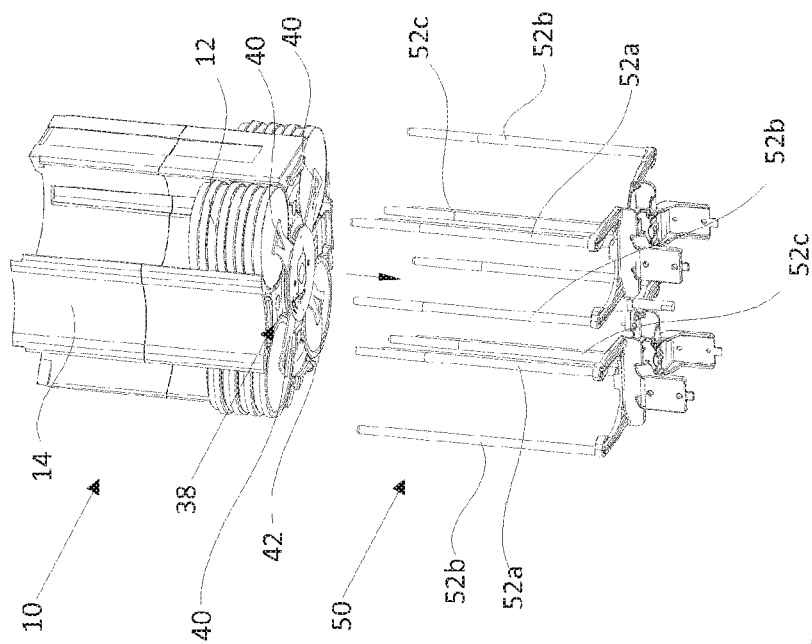

HOLDER FOR RECEIVING AND STORING LABORATORY VESSELS

BACKGROUND OF THE INVENTION

The invention relates to a holder for receiving and storing laboratory vessels for samples, microorganisms, cell cultures or the like, with a housing, at least one receptacle for the laboratory vessels, which receptacle extends along a loading axis (L) in the housing and into which the laboratory vessels can be introduced and can be stacked on top of each other therein.

A vast number of holding devices exist in the prior art which are used for transporting and storing laboratory vessels, in particular petri dishes. Their shape makes petri dishes ideally suited for stacking. In incubators but also in more complex devices for analyzing and evaluating samples, a plurality of stacks of petri dishes can usually be stored simultaneously in magazines provided for this purpose.

Various petri dish holders are known which have a housing comprising four receptacles arranged in a star-shaped configuration with parallel longitudinal axes. For storing and transport, petri dishes are loaded into the receptacles from above and stacked concentrically on top of each other therein. After transport, the petri dishes are then also unloaded from above. The receptacles are of a part-circular design and open on their sides which face away from each other. The openings usually extend over less than half of the circular arc so as to prevent the inserted petri dishes from falling out.

In practice, however, the loading and unloading of such holders proves impractical most of the time. Individual petri dishes or small groups thereof need to be removed from, or introduced into, one receptacle after the other. With increasing height of a stack of petri dishes to be moved simultaneously, there is also an increased risk of the stack becoming instable and the petri dishes shifting in place or even falling down. Moreover, this activity is often carried out manually, which is both monotonous and strenuous for the user.

A generic holder for receiving and holding laboratory vessels is known from EP 0 242 114 A2. The discharge opening is provided with catches which prevent the laboratory vessel from moving out of the holder. The catches are preloaded into their closed position by springs. The laboratory vessels can be unloaded through the unloading opening by pivoting the catch into its open position by means of a mechanism, in which position it will then expose the unloading opening. For this purpose, the catch is designed as a rocker arm whose end which is remote from the catch is engaged by a pusher to permit opening. Once the pusher has released the catch, the catch will be retained in its closed position by the spring. However, it will still be possible to insert a laboratory vessel from below towards the top against the spring force of the catch, which vessel will thus overcome the spring force and a certain lift height which essentially corresponds to a lever arm of the catch. This catch-based locking mechanism is very error-prone and of a very large design.

EP 0 242 114 A2 discloses a holder for receiving and storing laboratory vessels which has catches at its bottom unloading opening. The catches can be pivoted about an axis of rotation which is perpendicular to the unloading direction. When pivoted, the catches are either pressed upward by means of a pin or opened by a lifting device adapted to lift the laboratory vessel. This closure mechanism is also very error-prone and large in design.

DE 103 01 446 A1 discloses a holder for receiving and storing laboratory vessels. This holder has a single receptacle for laboratory vessels and a closure mechanism. This closure mechanism consists of pivotable locking catches which close the loading opening. The unloading opening is arranged laterally.

SUMMARY OF THE INVENTION

It is the object of the invention to provide a holder for receiving and storing laboratory vessels which does not have the abovementioned shortcomings and which allows one or plural stacks of petri dishes stored in it to be simultaneously loaded into a suitable device and one or plural stacks of petri dishes to be simultaneously unloaded from a suitable device and which is of a space-saving design.

This object is achieved by the characterized features of claim 1 in combination with the features of its preamble. The dependent claims relate to advantageous embodiments of the invention.

In a known manner, a holder for receiving and storing laboratory vessels for samples, microorganisms, cell cultures or the like comprises a housing and at least one receptacle for the laboratory vessels, which receptacle extends along a loading axis in the housing. The laboratory vessels can be introduced into the receptacle and can be stacked on top of each other therein, and the receptacle in the housing has a loading opening at the top to permit loading. On an underside arranged remote from the loading opening, the receptacle has an unloading opening which can be closed by means of a closure mechanism arranged in the housing. This allows one or plural stacks of laboratory vessels stored in the holder to be simultaneously introduced into a magazine of a device and left there after opening of the closure mechanism and removal of the holder. Similarly, an empty holder can be introduced into a device magazine loaded with one or plural stacks of laboratory vessels and removed with the petri dishes after closure of the closure device. This allows a large number of petri dishes to be transported safely and to be simultaneously loaded into, or removed from, a magazine or the like.

According to the inventive design, the closure mechanism is provided with a slide, which slide is movable to the unloading opening into a closing position to permit closure, and is movable from the unloading opening into an opening position to permit opening. A slide is basically a locking fitting which is displaced in a plane that essentially extends perpendicular to the material flow to be blocked, in the present case the petri dishes. One advantage of a slide compared to the known catches is its flat design and the fact that it is easy to control and drive. Closure mechanisms of this type are hardly prone to errors, are of a flat design and are easy to install.

In one embodiment of the invention, a transmission is provided which cooperates with the slide. This allows the movement of the slide to be adjusted and controlled precisely. Moreover, this can also be coupled with automatic devices or other means for loading and unloading the holder.

Preferably, a plurality of receptacles with associated loading and unloading openings is provided, and each unloading opening is associated with a slide. In this way, the holder can simultaneously receive or discharge a plurality of stacks of laboratory vessels. This increases the efficiency of the holder.

The individual slides of a holder can be coupled to each other in such a way that all slides can be moved simultaneously by a single drive. This allows several laboratory vessels from different receptacles to be released easily with one single opening movement of all slides. For this purpose, a common drive is also provided. Alternatively, however, an embodiment can also be provided in which the slides are controlled individually.

It is considered advantageous for the closure mechanism to rotatably move the slide from a closing position into an opening position thereof, and vice versa. Consequently, the movement required to displace the slide from its closing position to its opening position and vice versa only has a small angle compared to the movement for covering the laboratory vessel, thus making the closure mechanism very efficient.

Alternatively, a closure mechanism can also be provided which translationally moves the slide from its closing position to its opening position, and vice versa.

It is advantageous for the closure mechanism to be operable from the bottom where the unloading opening is. Operating the closure mechanism for opening and closing can thus be connected intuitively to the movement direction and the state—loaded or unloaded—of the holder and coupled to other working steps within a device in a simple way.

To achieve good integration into an automated or semi-automated system, the closure mechanism can have a drive hub or a carrier which can be used to operate the driving mechanism by a motor or manually, in particular by means of an operating handle engaging the drive hub or the carrier.

Preferably, the receptacle has a circular or at least part-circular base area. This makes it well suited for the introduction of petri dishes which are frequently used in biology and related areas and can be stacked easily.

In yet another aspect of the invention, the loading and unloading openings are concentrically arranged relative to each other such that the loading axis extends perpendicular to the loading opening and the unloading opening and in particular extends parallel to a longitudinal axis of the holder. As a result, loading, storage and unloading are performed along a single axis, thus minimizing the danger of a laboratory vessel shifting in place or becoming jammed unintentionally.

It is expedient to have a carrier handle provided at the top of the housing, which handle is in particular mounted so as to be retractable into the housing. First of all, this allows the holder to be conveniently carried using the carrier handle. Secondly, the holder, with the carrier handle retracted, can be accommodated in smaller places than would be possible if its carrier handle were fixed. This means higher flexibility when using the holder.

In particular, the carrier handle can be adapted to be completely retracted into the housing so that it will not project beyond an envelope of the housing. Consequently, extremely little space is required for accommodating the holder.

In a preferred embodiment, the holder is made of a heat-resistant material which allows autoclaving of the holder. This facilitates sterilization of the holder.

In one embodiment of the invention, it has proven advantageous for drain grooves that are open at least towards the underside of the holder to be provided along the longitudinal axis of the receptacle for the laboratory vessels. This makes it easier to drain fluids entering during use, thus avoiding fluid build-up in the holder.

In an alternative embodiment of the invention, engagement recesses are provided at least in the area of the unloading and/or loading openings, into which racks can be retracted to allow them to receive the laboratory vessels once the holder is withdrawn. This results in a simple, safe and stable unloading of the laboratory vessels.

It is expedient to have the engagement recesses provided in the form of through bores oriented parallel to the loading axis or as lateral grooves which are open towards the receptacle for the laboratory vessels. Their orientation parallel to the loading axis reduces the risk of unintentional shifting or jamming of the laboratory vessels during removal, and it facilitates the positioning of the racks.

In another aspect of the invention, mutually matching projections and recesses are provided at the top and at the bottom so that these projections and recesses will engage each other if plural holders are vertically stacked and will thus essentially be fixed in a positive-locking manner normal to the longitudinal axis. This positive fit prevents slipping of holders stacked on top of each other, making their use safer.

In yet another improved design, the projections and associated recesses are formed in such a way that a plurality of holders can be stacked concentrically relative to each other. Concentric stacking affords maximum stability and minimizes the required base area.

Preferably, the housing is made by plastic injection molding, in particular as a solid injection-molded part. Such a housing can be manufactured at low cost according to individual requirements and is easy to clean.

Similarly, the carrier handle can be made by plastic material injection molding, in particular as a solid injection-molded part. Here, too, low production costs and easy cleaning are an advantage.

Preferably, the loading and unloading openings are arranged concentrically relative to each other, in particular also concentrically relative to a loading direction and/or unloading direction.

It is expedient for the housing to have a label holder for inserting a label. This serves to protect labels which can be inserted by the user for easier identification of a holder.

In one embodiment of the invention, it has proven advantageous to provide identification, associated with a respective loading opening, for each receptacle, in particular at the top of the housing, which identification clearly identifies each receptacle of the laboratory vessels. More specifically, such identification is provided in the form of a recess or a depression. This makes it easier to visually distinguish receptacles loaded with different samples, and it also facilitates the allocation of respective receptacles of a plurality of vertically stacked holders to each other.

In a preferred embodiment of the invention, the pairs of slides can be coupled via a transmission, in particular of the planetary type, and can be connected to a drive. The transmission can comprise gears which mesh with the pairs of slides. The gears are in particular mounted on a basic body and are made to rotate by the drive. Rotation of the drive displaces the pairs of slides from an opening position to a closing position thereof which latter can be limited by stops. As actuating means, a device centrically mounted in the basic body can be provided which consists of the centering means and a cantilever and is preferably connected to a drive which is mounted in particular on the loading and unloading station. This yields a high degree of automation of the closure mechanism.

Additional advantages, features and possible applications of the present invention can be gathered from the description which follows, in combination with the embodiments illustrated in the drawings.

Throughout the description, the claims and the drawings, those terms and associated reference signs are used as are listed in the List of Reference Signs below. In the drawings,

BRIEF DESCRIPTION OF THE DRAWINGS

FIG. 2a is a bottom view of the holder with petri dishes inserted therein and slides moved into their closing position;

FIG. 2b is a bottom view of the holder with slides moved into their opening position;

FIG. 3a is a perspective view of the loaded holder and a rack; and

FIG. 3b is a perspective view of the holder and the loaded rack.

DETAILED DESCRIPTION OF THE INVENTION

Figure 1:
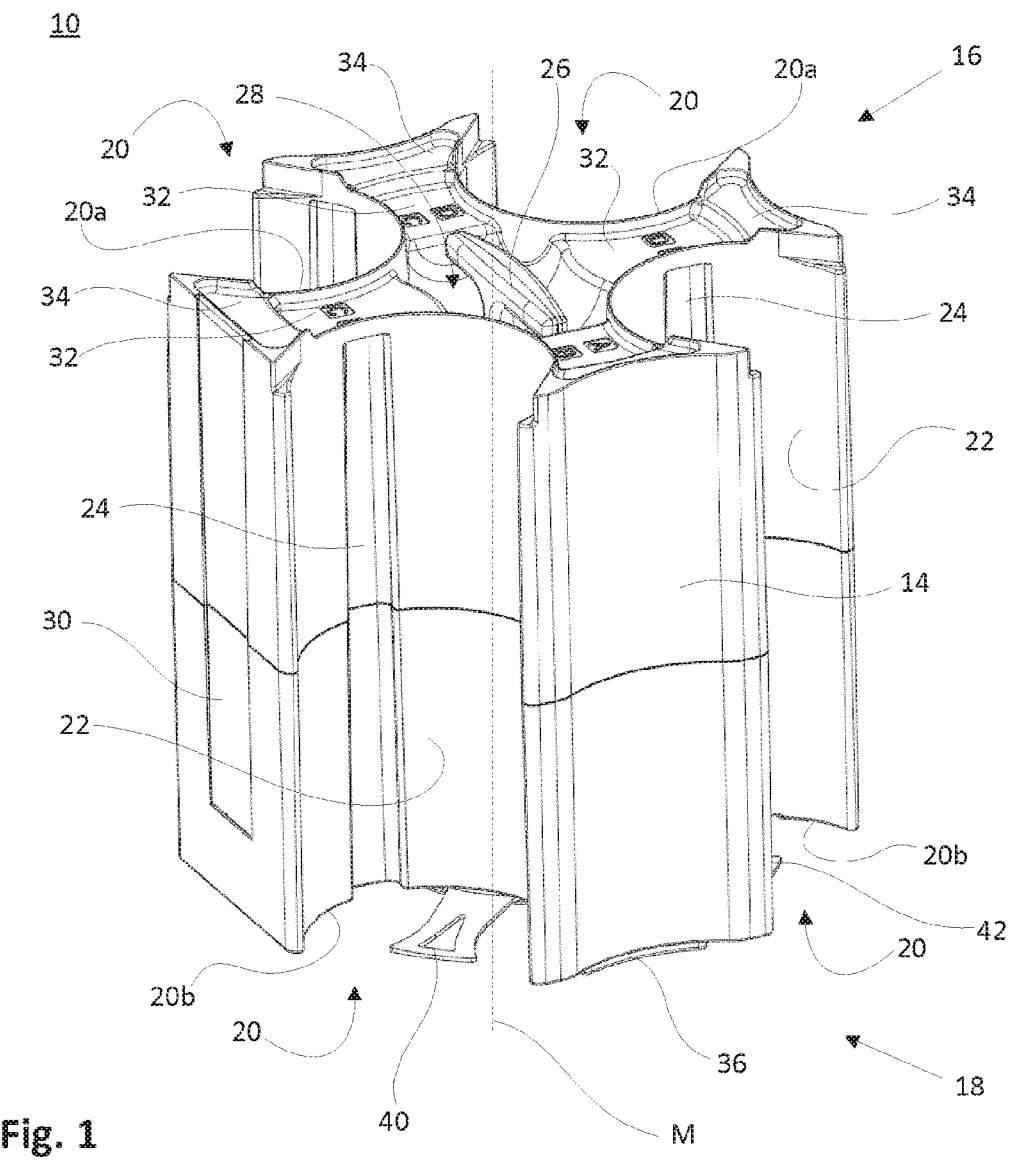
FIG. 1 is a perspective view of a holder according to the invention.

FIG. 1 is a perspective view of a holder 10 according to the invention for storing and transporting petri dishes as shown in FIG. 2a.

The carrier 10 has a housing 14 with a central axis M, an upper side 16 and an underside 18 opposite to the upper side 16.

Formed in the housing 14 are four receptacles 20 for petri dishes which extend between the upper side 16 and the underside 18 parallel to the central axis M. Each receptacle 20 has a wall 22 formed by the housing 14 and having a part-circular cross-section and which is open along its entire longitudinal extension on the side facing away from the central axis M. The receptacles 20 are both open towards the upper side 16 where they each have a loading opening 20a for loading the holder 10 with petri dishes, and towards the underside 18 where they each have an unloading opening 20b for unloading the petri dishes. Of course, it is also possible to unload petri dishes via the loading opening 20a and to load them via the unloading opening 20b.

Each wall 22 has two grooves 24 each in it which are parallel to the central axis M and open towards the underside 18. The grooves 24 are adapted to permit engagement of rods of a rack described with reference to FIGS. 3a and 3b.

Provided on the exterior of the housing 14 is a label holder 30 which extends parallel to the central axis M and is open toward the top 16. A label can be inserted in this label holder 30 for safely identifying the holder 10.

On the upper side 16, an extensible carrier handle 26 is provided. This view shows the carrier handle 26 in its retracted state in which it is inserted into a centrally located retraction opening 28 so as to save space.

For the convenient transport of the holder 10, the carrier handle 26 can be pulled out of the retraction opening 28.

Furthermore, eight recesses 32 are provided on the upper side 16 of the housing 14 which are arranged in pairs each between two loading openings 20a for clearly identifying each receptacle 20. For this purpose, the two recesses 32 which directly abut on the same loading opening 20a are marked with the same letter A, B, C or D. Instead of letters, numbers, symbols or colors can also be used.

Adjacent to each of the four pairs of recesses 32, a recess 34 each is provided radially further outwards on the upper side 16. Matching the recess 34, a projection 36 is provided on the underside 18 of the housing 14. When a plurality of holders 10 are stacked on top of each other, the projections 36 will engage the recesses 34 so as to obtain a positive connection between the projections 36 and the recesses 34. A plurality of holders 10 can thus be stacked on top of each other in a stable manner.

On the underside 18 of the housing 14, slides 40, 42 are provided for opening and closing the unloading openings 20b. The slides 40, 42 are described in more detail with reference to FIGS. 2a and 2b.

FIG. 2a is a bottom view of the holder 10 with petri dishes 12 loaded into the receptacles 20 and the closure mechanism 38 in its closing position, in which the petri dishes 12 are covered by the slides 40, 42.

The slides 40, 42 are arranged in pairs and offset from each other concentrically relative to the central axis M of the housing 14. The slide pairs 40, 42 are coupled via a transmission 44, in particular of the planetary type, and can be connected to a drive. The transmission 44 comprises gears 46, 48 which mesh with the slide pairs 40, 42. The gears 46, 48 are mounted on a basic body and are made to rotate by the drive. Rotation of the drive causes the slide pairs 40, 42 to move from an opening position to a closing position thereof, which latter is limited by stops. As operating means, a device centrally mounted in the basic body can be provided which consists of the centering means and a cantilever and is preferably connected to a drive which is in particular located at a loading and unloading station.

FIG. 2b is a bottom view of the holder 10 in an unloaded state thereof in which the slide pairs 40, 42 are in their opening position, exposing the unloading openings 20b.

FIG. 3a is a view of the holder 10 loaded with petri dishes 12, similar to the view of FIG. 2a, before it is introduced into a rack 50.

In the rack 50, three rods 52a, 52b, 52c are provided for the stable storage of a stack of petri dishes 12, which rods are uniformly spaced from each other with respect to the circumference of the petri dishes 12. When the holder 10 is inserted in the magazine, two rods 52a, 52b each will engage the grooves 24 described with reference to FIG. 1 and made in the wall 22 of the respective receptacle 20. The respective third rod 52c will be located at the position where the associated receptacle 20 is open on its side facing away from the central axis M.

FIG. 3b is a view of the holder 10 in an unloaded state thereof, similar to the view of FIG. 2b, following its introduction into the rack 50. The petri dishes 12 are now stored between the rods 52a, 52b.

Owing to the fact that the unloading opening 20b is arranged remote from the loading opening 20a on the underside 18 of the holder 10, a plurality of complete stacks of petri dishes 12 can be inserted simultaneously into a rack 50 and left there, for example following transport from a storage place to an analysis device, after operating a closure mechanism comprising the transmission 44 and the gears 46, 48 and moving the slides 40, 42 into an opening position thereof. The stability of the stack arrangement will not be jeopardized at any time and the petri dishes 12 will remain in the rack 50 after removal of the holder 10.

Although the present invention has been fully described in connection with the preferred embodiments thereof with reference to the accompanying drawings, it is to be noted that various changes and modifications will be apparent to those skilled in the art. Such changes and modifications are to be understood as included within the scope of the present invention as defined by the appended claims, unless they depart therefrom.

LIST OF REFERENCE SIGNS 10 holder
12 petri dishes
14 housing
16 upper side
18 underside 20 receptacles
20a loading opening
20b unloading opening
22 wall
24 groove
26 carrier handle
28 retraction opening
30 label holder
32 depression
34 recess
36 projection
38 closure mechanism
40, 42 slide
44 transmission
44a gearing
46, 48 gears
50 rack
52a,b,c rods
M central axis
L loading axis

The invention claimed is:

1. A holder structure for receiving and storing laboratory vessels for at least one of samples, microorganisms, and cell cultures, the holder structure comprising: a holder and a rack,
wherein the holder includes a housing, and a plurality of receptacles for receiving the laboratory vessels, each of the plurality of receptacles extending along a loading axis (L) in the housing and into which the laboratory vessels can be introduced and can be stacked on top of each other therein, wherein each of the plurality of receptacles in the housing has a loading opening to permit loading, wherein on an underside arranged remote from the loading opening, each of the plurality of receptacles has an unloading opening which can be closed by means of a closure mechanism arranged in the housing, wherein the rack is operatively formed to receive the laboratory vessels thereinto from the holder, the rack including a plurality of rods to be removably connectable with the holder,
wherein the closure mechanism is provided with a slide, the slide being movable to the unloading opening into a closing position to permit closure and movable from the unloading opening into an opening position to permit opening, and the closure mechanism rotationally moving the slide to and from the closing position and the opening position thereof, wherein the closure mechanism is operatively connectable to a drive mechanism from the underside of the holder, such that the drive mechanism drives the rotational moving of the slide to and from the closing and opening positions, and
wherein the housing is further formed with a plurality of walls between and defining each of the plurality of receptacles, each of said plurality of walls being formed with a vertically-extending groove defined on a sidewall portion to receive the plurality of removably connectable rods of the rack, an upper wall portion of each of the plurality of walls being formed with a shaped recess, and a bottom wall portion of each of the plurality of walls being formed with a shaped projection to removably fit with a corresponding shaped recess of another holder connectably aligned underneath, the bottom wall projections and associated upper wall recesses being formed so as to allow a plurality of holders to be stacked concentrically with each other.

2. A holder according to claim 1, characterized in that a transmission is provided which cooperates with the slide.

3. A holder according to claim 1, characterized in that several receptacles with associated loading and unloading openings are provided and that the slide is associated with each unloading opening.

4. A holder according to claim 3, characterized in that the slides are coupled to one another such that all slides can be moved simultaneously by a single drive.

5. A holder according to claim 1, characterized in that the closure mechanism translationally moves the slide to and from the closing position into the opening position thereof.

6. A holder according to claim 1, characterized in that the closure mechanism has a drive hub or a carrier on the underside to operate the drive mechanism by a motor or manually by means of an operating handle engaging the drive hub or the carrier.

7. A holder according to claim 1, characterized in that the receptacle has a circular or part-circular base area.

8. A holder according to claim 1, characterized in that the loading opening and the unloading opening are arranged concentrically to each other such that the loading axis (L) extends perpendicular to the loading opening and the unloading opening and runs parallel to a longitudinal axis of the holder.

9. A holder according to claim 1, characterized in that a carrier handle is provided which is arranged on an upper side of the housing, wherein the handle is mounted so as to be retractable into the housing.

10. A holder according to claim 9, characterized in that the carrier handle is completely retractable into the housing so as to not project beyond an envelope of the housing.

11. A holder according to claim 1, characterized by a heat-resistant material which allows the holder to be autoclaved.

12. A holder according to claim 1, characterized in that engagement recesses are provided at least in the area of the unloading opening and/or the loading opening, wherein the racks, which are adapted to receive the laboratory vessels after withdrawal of the holder, are retractable into the recesses.

13. A holder according to claim 1, characterized in that engagement recesses are provided in the form of through bores which extend parallel to the longitudinal axis, or as lateral grooves which are open toward the receptacle for the laboratory vessels.

14. A holder according to claim 1, characterized by the formation of the housing produced in a plastic injection molding process as a solid injection-molded part.

15. A holder according to claim 1, characterized in that on the side of the housing, a label holder is provided for insertion of a label.

16. A holder according to claim 1, characterized in that for each receptacle, an identification associated with the respective loading opening is provided on the upper side of the housing, wherein the identification identifies the receptacle of the laboratory vessels and is provided in the form of a recess or a depression.

* * * * *